United States Patent [19]
Berg et al.

[11] Patent Number: 5,792,116
[45] Date of Patent: Aug. 11, 1998

[54] CATHETER HAVING GEOMETRICALLY SHAPED SURFACE AND METHOD OF MANUFACTURE

[75] Inventors: Todd A. Berg, Lino Lakes; Thomas J. Bachinski, Lakeville; Richard R. Prather, Rogers, all of Minn.

[73] Assignee: SciMed Life Systems, Inc., Maple Grove, Minn.

[21] Appl. No.: 855,223

[22] Filed: May 13, 1997

Related U.S. Application Data

[63] Continuation-in-part of Ser. No. 442,815, May 17, 1995, Pat. No. 5,647,846.

[51] Int. Cl.$^6$ .................................................. A61M 25/00
[52] U.S. Cl. .................... 604/282; 604/280; 604/264; 604/93; 128/772; 606/194
[58] Field of Search .................. 604/282, 95–103, 604/281, 283, 264–5, 93, 164; 606/191–192, 194; 128/772

[56] References Cited

U.S. PATENT DOCUMENTS

| | | | |
|---|---|---|---|
| 3,731,671 | 5/1973 | Mageoh | 128/2.05 |
| 3,944,641 | 3/1976 | Lemelson | 264/70 |
| 4,330,497 | 5/1982 | Agdanowski | 264/150 |
| 4,430,083 | 2/1984 | Ganz et al. | 604/283 |
| 4,516,970 | 5/1985 | Kaufman et al. | 604/270 |
| 4,755,176 | 7/1988 | Patel | 604/280 |
| 4,790,831 | 12/1988 | Skribiski | 604/282 |
| 4,801,297 | 1/1989 | Mueller | 604/280 |
| 4,832,028 | 5/1989 | Patel | 128/344 |
| 4,840,623 | 6/1989 | Quackenbush | 604/280 |
| 4,863,441 | 9/1989 | Lindsay et al. | 604/280 |
| 5,122,125 | 6/1992 | Deuss | 604/282 |
| 5,125,909 | 6/1992 | Heimberger | 604/264 |
| 5,334,169 | 8/1994 | Brown et al. | 604/282 |
| 5,360,414 | 11/1994 | Yarger | 604/264 |
| 5,364,344 | 11/1994 | Beattie et al. | 604/43 |
| 5,364,356 | 11/1994 | Hofling | 604/96 |
| 5,496,292 | 3/1996 | Burnham | 604/282 |

FOREIGN PATENT DOCUMENTS 462423   1/1914   France.

*Primary Examiner*—Mark Bockelman
*Assistant Examiner*—N. Kent Gring
*Attorney, Agent, or Firm*—Crompton, Seager & Tufte, LLC

[57] ABSTRACT

Catheter and method of manufacturing such catheter. The catheter includes an elongate shaft having an interior lumen extending therethrough. The interior surface of the lumen is geometrically configured to reduce friction and increase catheter performance. Additionally, the geometrically configured inside surface allows dye or blood to perfuse past the distal end of the catheter when engaged in the coronary artery. The catheter may also include a geometrically configured outer surface at its distal end having perfusion channels to allow blood to perfuse past the distal end of the catheter during catheter engagement.

13 Claims, 7 Drawing Sheets

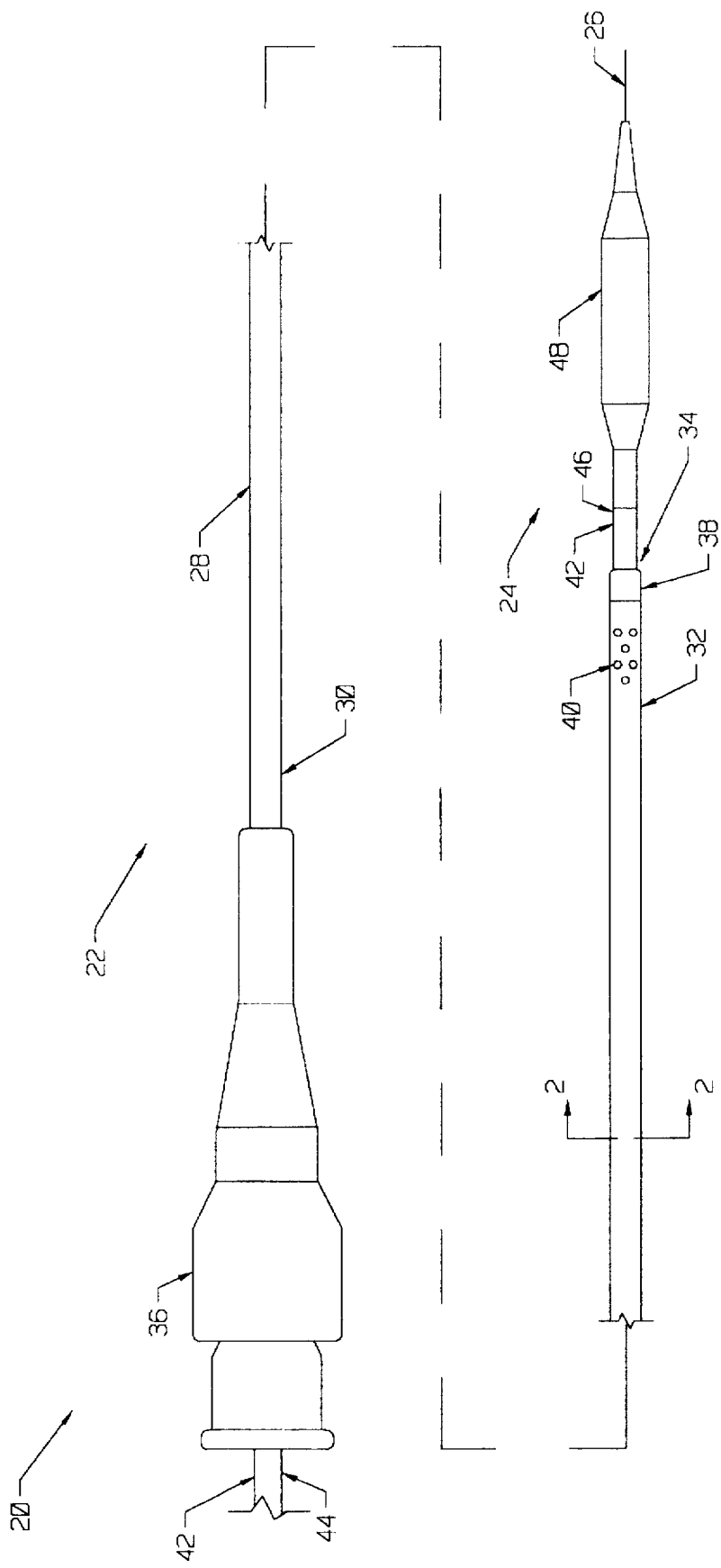

CATHETER HAVING GEOMETRICALLY SHAPED SURFACE AND METHOD OF MANUFACTURE

CROSS REFERENCE TO CO-PENDING APPLICATIONS

This application is a continuation-in-part of U.S. Ser. No. 08/442,815, filed May 17, 1995, entitled "Catheter Having Geometrically Shaped Surface and Method of Manufacture", now U.S. Pat. No. 5,647,846, to the same assignee as the present application.

FIELD OF THE INVENTION

The present invention relates to guide catheters and diagnostic catheters used in medical catheterization procedures and a method of manufacturing such catheters. In particular, the present invention relates to an improved guide or diagnostic catheter of a simple, braided or braidless catheter design, having a geometrically configured inside or outside diameter to reduce friction and to allow radiopaque dye or blood to perfuse past the distal end of the catheter into the coronary artery. In one embodiment, the geometrically configured inside surface reduces friction and provides a larger catheter lumen allowing for easier passage of treatment devices therethrough.

Description of the Prior Art

Guide catheters and diagnostic catheters are well known for use in coronary catheterization and percutaneous transluminal coronary angioplasty (PTCA) procedures. Guide catheters aid in treatment of arterial lesions by providing a conduit for positioning dilatation balloon systems across an arterial stenosis. Guide catheters and diagnostic catheters work with various assemblies for performing other medical, therapeutic, and diagnostic procedures, such as dye delivery, arterial flushing, or arterial pressure monitoring.

Diagnostic catheters are used during cardiac catheterization for diagnosis of coronary artery disease in order to define vessel anatomy, isolate lesions, and identify adjacent cardiac branches which may impinge on the lesion and affect ventricular function.

For diagnosis of the coronary artery, the femoral artery is entered percutaneously and a sheath is inserted into the artery to provide access to the patient's vascular system. The diagnostic catheter is inserted into the femoral artery through this introducer sheath over a guide wire and advanced up the aorta to the aortic arch. Once over the aortic arch, the guide wire may be removed. A Y-adapter and manifold assembly are attached to the diagnostic catheter for implementation of diagnostic procedures, such as dye delivery, flushing capabilities, and arterial pressure monitoring.

The diagnostic catheter design generally includes a shaft having a proximal and a distal end. A lumen extends longitudinally through the shaft from the proximal to the distal end. Operably connected to the proximal end of the shaft is a hub assembly, for connection to catheterization equipment, and connected to the distal end of the shaft is a soft tip.

The distal end of the diagnostic catheter shaft is shaped to access the ostium of the coronary artery having the stenotic lesion. Different shapes may be employed for access to the ostium of a right or left coronary artery, mammary artery or the ostium of a bi-pass vein. During the diagnosis procedure, the physician advances and maneuvers the diagnostic catheter shaft within the artery, while at the same time injecting dye. The physician observes the dye using an angiography monitor for visualization of the patient's coronary system.

The diagnostic catheter is advanced and maneuvered until the distal end is properly engaged in the ostium of the coronary artery the physician believes to contain the stenosis. Once seated in the ostium, the physician injects additional dye for observations of obstruction to dye flow, indicative of the coronary disease.

For treatment of the coronary disease through angioplasty or other catheter based treatments, guide catheters are used. The guide catheters provide access to the area within the arterial system containing the stenotic lesion, and support for the treatment catheter which often includes a balloon dilatation system. Guide catheters are similar in construction to diagnostic catheters, although they are generally larger in size. Prior art guide catheters typically have a pre-shaped distal section or tip region to aid in access to the ostium of the coronary artery to receive treatment.

In operation, the guide catheter is introduced over a guide wire through a previously placed femoral introducer sheath and advanced up to the aortic arch. The guide wire can then be removed, and the guide catheter can be advanced and maneuvered until the guide catheter soft tip is properly engaged in the ostium of the coronary artery to be dilatated. A Y-adapter and manifold assembly are attached to the guide catheter hub at the proximal end for implementation of therapeutic procedures, such as dye delivery, flushing capabilities, pressure monitoring and delivery of the dilatation balloon system.

During angioplasty procedures, the catheters must be able to traverse tortuous pathways through blood vessels to the stenosis in a manner as atraumatic as possible. Therefore, to limit insertion time and discomfort to the patient, the catheter must be stiff enough to resist the formation of kinks, while at the same time the catheter must possess flexibility to be responsive to maneuvering forces when guiding the catheter through the vascular system. It is important that the guide catheter exhibit good torque control such that manipulation of a proximal portion of the guide catheter is responsively translated to the tip or distal end of the catheter to curve and guide the catheter through the tortuous pathways.

To meet the above performance requirements, guide catheters and diagnostic catheters are manufactured using polymers in conjunction with a braid of high-strength fibers or stainless steel wires incorporated into the tube. The guide catheters are generally formed of three layers: a first inner layer commonly formed of polytetrafluoroethylene to decrease the coefficient of friction between a balloon catheter and the guide catheter; a middle layer consisting of braided wire for torque control; and a third, outer layer commonly formed of polyether blocked amide, polyethylene, polyurethane or a nylon-blend for stable positioning of the guide catheter, and providing backout support during other treatment procedures.

Additionally, guide catheters may include perfusion ports at their distal end. The perfusion ports allow perfusion of blood into a coronary artery when the distal end of the guide catheter is engaged within the ostium of the coronary artery to be dilatated.

An important function of the internal lumen surface of the catheter lumen is to provide very low surface friction between the catheter and the treatment device. The low friction internal surface facilitates advancement of treatment devices through the catheter lumen, which is especially critical in the curved portion of the catheter. A low friction surface is achieved by using materials, such as lubricous polymers, as the internal surface material. One preferred material is polytetrafluoroethylene. The low friction characteristics of polytetrafluoroethylene provide minimal surface friction between the internal surface of the catheter lumen and the advancing treatment device.

Problems exist with the use of lubricous polymers, such as polytetrafluoroethylene, as the inner layer in catheter designs. The use of such inner layers result in increased costs, reduced catheter curve retention performance, and additional manufacturing time. The polytetrafluoroethylene inner layer requires a separate special extrusion process and etching. The polytetrafluoroethylene inner layer material also takes away from the shaft material in terms of total volume, which affects curve retention, back-up support, and radiopacity. Additionally, difficulties arise in manufacturing with the adhesion of the polytetrafluoroethylene material to the catheter shaft material.

It is desirable to eliminate the lubricous polymer inner layer, commonly formed of polytetrafluoroethylene, while maintaining or improving low surface friction properties. Particularly, it is desirable to have a diagnostic or guide catheter design which minimizes the co-efficient of friction between the guide catheter inside surface and a treatment device, such as a balloon catheter. It is desirable to have a catheter design which does not require an additional lubricous inner layer for reducing the co-efficient of friction between the catheter and a treatment device.

Additionally, it is desirable in catheter design which allows the inside diameter of the diagnostic or guide catheter to be maximized relative to the outside diameter, providing maximum space for dye flow and dilatation catheter delivery. It is also desirable for a catheter to have a thicker outer layer for providing additional back-out support, curve retention and radiopacity during a catheter procedure.

Yet another desirable characteristic in guide catheter design is to allow for dye flow or perfusion of blood past the distal end of a guide catheter having its distal end engaged within the ostium of a coronary to be dilatated, during a catheter procedure.

While designing catheters to meet these design goals, the catheters must continue to meet performance requirements of kink resistance, curve retention, column strength, and torque control for advancement within the patient's vascular system.

U.S. Pat. No. 5,334,169 to Brown et al. suggests a reinforced catheter with thin monolithic walls having interior walls which are channeled in a rifled, spiraled or axial configuration to trap resistance particles and decreased friction resistance. Although the rifled channels reduce the surface area contact with a treatment device extending through the catheter, friction is only greatly reduced for movement of the treatment device in an axial direction and not a longitudinal direction relative to the catheter shaft. Additionally, the channel configuration suggested by Brown et al. does not improve catheter performance for blood perfusion or dye delivery.

U.S. Pat. No. 4,840,623 to Quackenbush suggests a medical catheter with splined internal wall. The splined internal wall is of a high durometer having sufficient rigidity for improved transmission of torque from the proximal end to the distal end of the catheter during angioplasty procedure. The splined internal wall provides structural integrity to the catheter instead of the use of catheters having a braided middle layer.

SUMMARY OF THE INVENTION

The present invention relates to a guide or diagnostic catheter capable of performing the function of conventional diagnostic and guide catheters.

In particular, the present invention relates to a catheter having a geometrically configured inside diameter to reduce friction and to allow dye or blood to perfuse past the distal end of the catheter into the coronary artery.

In one preferred embodiment, the catheter of the present invention is for use as a guide or diagnostic catheter in catheter procedures. The catheter includes a generally elongate shaft having a proximal end and a distal end. At least one lumen extends longitudinally between the proximal end and the distal end of the shaft.

The shaft includes an inner layer having a tubular shape. The inner layer includes a geometrically configured inner surface having a plurality of channels spaced radially about the inner layer. The channels extend longitudinally along the length of the elongate shaft inner layer. Further, a treatment device may be located within the lumen, wherein the channels reduce friction when the treatment device is moved relative to the catheter shaft.

In one embodiment, the inner layer is formed of a polymeric material. The inner surface may be coated with a lubricant, such as silicone. Alternatively, the inner layer may be formed of a lubricous polymer, such as polytetrafluoroethylene.

The catheter shaft may include a plurality of openings located at the distal end of the catheter shaft. The plurality of openings are in communication with the lumen. The openings provide a perfusion path through the channels to a point distal of the catheter for perfusion of blood into the coronary artery when the catheter is engaged in the ostium of the coronary artery to receive treatment.

The catheter may include a perfusion section located at the distal end of the shaft having a plurality of channels disposed radially about the exterior surface thereof. The channels may extend longitudinally along the length of the section. The channels may allow perfusion of blood past the distal end of the catheter shaft, while the catheter is engaged in the ostium of the coronary to receive treatment.

In yet another embodiment, the present invention includes a method of manufacturing a catheter. The catheter has an elongate shaft including a proximal end, a distal end and a lumen extending between the proximal end and the distal end. The method includes the step of providing a mandrel having an outer surface geometrically configured to reduce friction. A first material is extruded over the mandrel. The mandrel is then removed. The first material may be a polymeric material. The geometrically configured surface may include a plurality of channels spaced axially about the mandrel, extending longitudinally along the length of the mandrel.

The method may further include extruding a second material over the mandrel. Alternatively, a plurality of strands may be wrapped over the first material, with a second material extruded over the strands.

Yet another embodiment of the present invention includes a catheter for use in guide or diagnostic catheter procedures. The catheter includes a generally elongate shaft having a proximal end and a distal end, with at least one lumen extending longitudinally therethrough. Means are provided for perfusion, positioned on the distal end of the shaft. The means for perfusion includes a perfusion sleeve having a plurality of channels positioned on the outer surface of the sleeve, the channels extending longitudinally along the length of the sleeve. The shaft may further include an inner layer having an inner surface which is geometrically configured to reduce friction. The sleeve may be formed integral the catheter shaft. Alternatively, the sleeve may be bonded to the catheter shaft.

The present invention provides an economically feasible diagnostic or guide catheter design. The catheter of the present invention is less costly to manufacture than conventional catheters since it uses geometry rather than material properties to provide a low friction surface for the internal lumen of the catheter.

BRIEF DESCRIPTION OF THE DRAWINGS

The invention will be further described with reference to the accompanying drawings where like numbers refer to like parts in several views and wherein:

FIG. 1 is a perspective view of a catheter in accordance with the present invention.

DETAILED DESCRIPTION OF THE PREFERRED EMBODIMENTS

Figure 3:
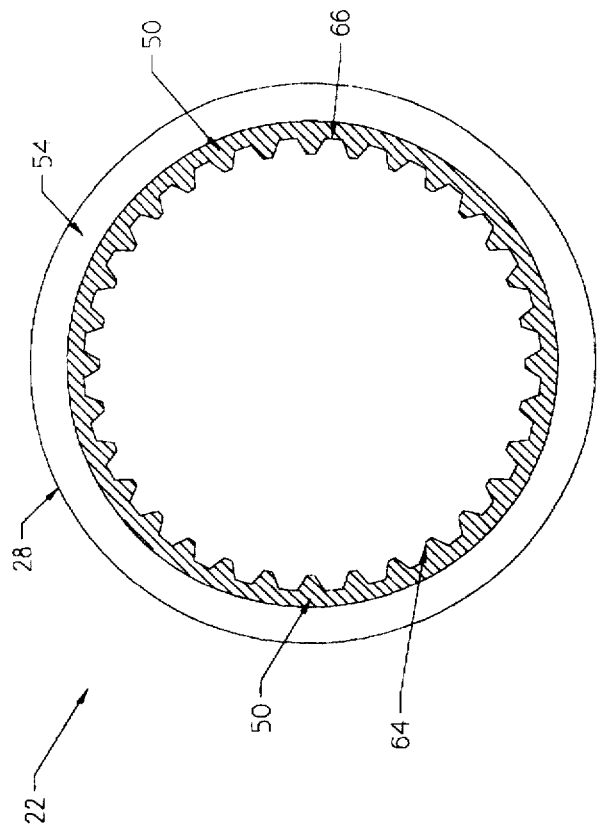
FIG. 3 is a cross-sectional view of an alternative embodiment of the catheter of FIG. 1.

The present invention relates to an improved guide or diagnostic catheter having a simple braided or braidless design having a lumen with a geometrically configured inner surface for increased catheter performance.

Although references throughout this specification may be specifically made to either guide catheters or diagnostic catheters, references made to one are equally applicable to both guide catheters and diagnostic catheters, coronary, neuro, general periphery, and vascular type catheters.

FIG. 1 shows a perspective view of a catheter assembly 20 in accordance with the present invention. In one preferred embodiment, the catheter assembly 20 includes a guide catheter 22 positioned over a treatment device, such as the balloon catheter 24 shown, for use in angioplasty procedures. Balloon dilatation catheter 24 is positioned over guide wire 26.

Guide catheter 22 includes a shaft 28 having a proximal end 30 and a distal end 32. A treatment lumen 34 (shown in cross section in FIG. 2) extends longitudinally through the shaft 28 from the proximal end 30 to the distal end 32. Operably connected to the proximal end 30 of the shaft 28 is a hub assembly 36 which communicates with treatment lumen 34 for connection to angioplasty treatment devices (not shown).

Located at the distal end 32 of the shaft 28 is soft tip 38. Soft tip 38 provides for atraumatic engagement of the ostium of the coronary receiving treatment. Additionally, perfusion openings 40 are located at the distal end 32 of shaft 28 for perfusion of blood into the coronary artery during ostial engagement.

Figure 2:
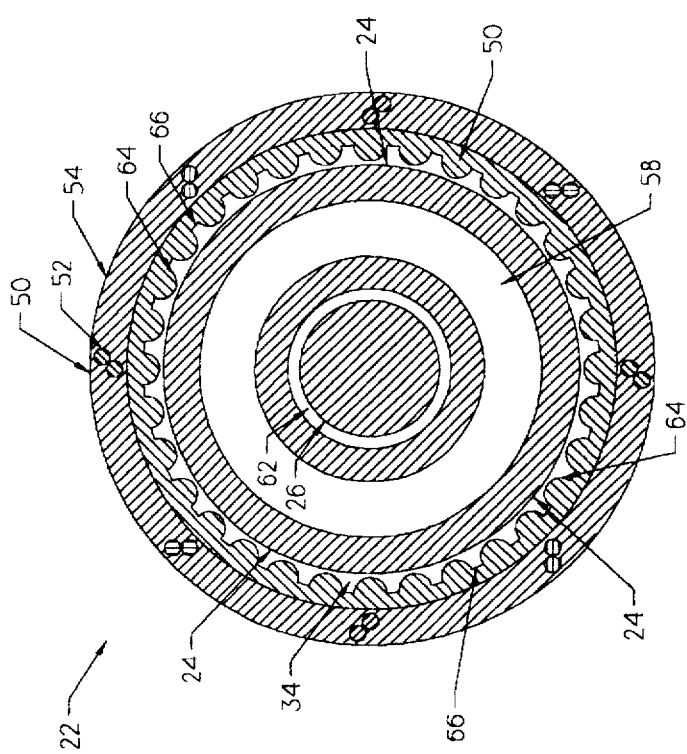
FIG. 2 is a cross-sectional view of the catheter of FIG. 1 showing a treatment device disposed therein.

Referring to FIG. 2, a cross section of catheter assembly 20 is shown taken along line 2—2 of FIG. 1. Guide catheter 28 is generally formed of three layers: a first inner layer 50 to decrease the co-efficient of friction between balloon catheter 24 and guide catheter 22; a middle layer 52 consisting of braided wire for kink resistance and torque control; and a third, outer layer 54 commonly formed of polyethylene, polyurethane, polyether block amide (PEBA) or a nylon-blend for stable positioning of the guide catheter 22 and providing back-out support during other treatment procedures.

Positioned within guide catheter 22 treatment lumen 34 is balloon dilatation catheter 24. Balloon dilatation catheter 24 includes a shaft 42 which is of a coaxial lumen design. Shaft 42 includes a proximal end 44 and a distal end 46. A dilatation balloon 48 is carried at the distal end of shaft 42. In one preferred embodiment, the balloon catheter 24 shaft 42 is formed of polyether block amide (PEBA), and is impregnated with a radiopaque material, such as barium sulfate or bismuth subcarbonate, to allow for partial visualization of the shaft 42 during the catheter procedure.

The coaxial lumen design of balloon catheter 24 includes an annular inflation lumen 58 in communication with balloon 48 and guide wire lumen 62 having guide wire 26 disposed therein. Similar to guide catheter 22 shaft 28, the balloon catheter 24 shaft 42 is usually impregnated with a radiopaque material, such as barium sulfate or bismuth subcarbonate, to allow for partial visualization of balloon catheter 24 during the catheter procedure.

Guide catheter 22 inner layer 50 includes a geometrically configured inner surface 64 to reduce the friction between catheter 22 and balloon catheter 24 during movement of the balloon catheter 24 relative to the catheter 22. In one preferred embodiment, the inner layer 50 is formed of polyether block amide (PEBA) for additional curve retention and back-up support. Additionally, inner layer 50 may be impregnated with radiopaque material, such as barium sulfate or bismuth subcarbonate, to allow for improved visualization of the catheter 22 during the catheter procedure.

Geometrically configured inner surface 64 of inner layer 50 eliminates the need for a lubricous polymer, such as polytetrafluoroethylene, as the inner layer 50 material. With geometrically configured inner surface 64, low surface friction properties are achieved through geometry rather than material properties, such as with the lubricous polymer.

In one preferred embodiment, the geometrically configured inner surface 64 includes a plurality of microchannels 66 spaced axially about the inner surface 64, which run the longitudinal length of the catheter shaft 28. Channels 66 reduce the contact surface area of the catheter inner surface 64 with the balloon catheter 24, minimizing the frictional resistance as balloon catheter 24 is moved relative to inner surface 64.

By using geometrically configured inner surface 64 channels 66, a low frictional resistance surface is obtained for the treatment lumen 34 without relying on the material properties of lubricous materials, such as polytetrafluoroethylene. The geometrically configured inner surface 64 of the present invention will significantly lower manufacturing costs by eliminating special extrusion processes associated with providing guide catheter 22 with a polytetrafluoroethylene inner layer and etching. Additionally, geometrically configured inner surface 64 eliminates problems associated with adherence of polytetrafluoroethylene to catheter shaft materials.

Geometrically configured inner surface 64 improves the performance of the catheter shaft 28. In conventional catheters, a lubricous polymer inner layer accounts for approximately twenty percent of the thickness of the guide catheter wall. With the present invention, a lubricous polymer inner layer is no longer necessary, allowing more shaft material to be used for guide catheter 22. The higher volume of shaft material increases catheter curve retention, back-up support, and radiopacity properties. Alternatively, the absence of a lubricous polymer inner layer may allow for maximizing the size of treatment lumen 34 relative to guide catheter 22, allowing for slidable reception of larger treatment devices within a catheter having a smaller outside diameter.

In the embodiment shown, channels 66 extend longitudinally the entire length of the guide catheter 22 shaft 28. Alternatively, it is recognized that most resistance between the guide catheter 22 and a treatment device occurs at the distal end of guide catheter 22 near the soft tip 38. It is recognized that channels 66 could be located only at the distal end 32 soft tip 38 region of guide catheter 22, increasing the performance of the guide catheter 22 soft tip 38 region.

It is also recognized that the inner layer 50, having a geometrically configured inner surface 64, can be formed of a lubricous material, such as a lubricous polymer, to increase the performance of guide catheter 22. In one preferred embodiment, the inner layer 50 inner surface 64 includes channels 66, and is formed of polytetrafluoroethylene for improving treatment device passage performance through guide catheter 22. Alternatively, inner surface 64 may be coated with a lubricant such as silicone.

Figure 4:
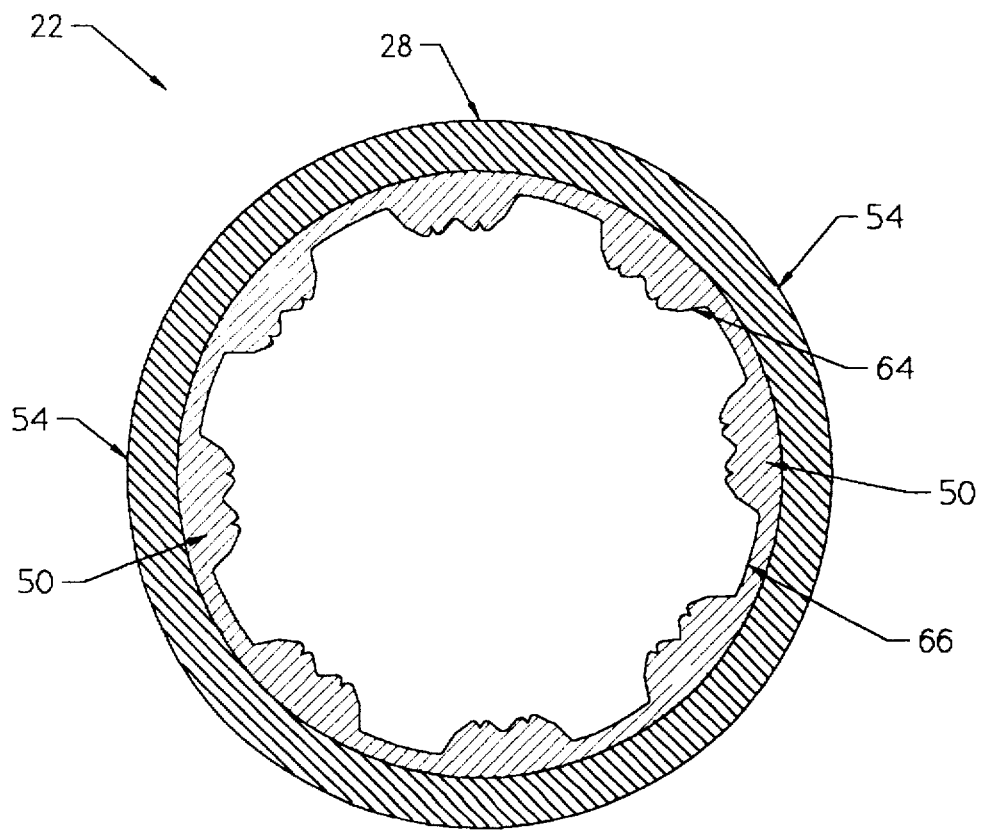
FIG. 4 is cross-sectional view of an alternative embodiment of the catheter of FIG. 1.

It is recognized that inner layer 50 inner surface 64 may take on alternate configurations while remaining within the scope of the present invention. Referring to FIGS. 3 and 4, alternate geometrically configured inner surfaces 64 are shown. In FIG. 3, inner surface 64 is generally trapezoidal shaped, and in FIG. 4, the inner surface 64 is formed of a non-uniform configuration. In both FIG. 3 and FIG. 4, the geometrical configuration of inner surface 64 includes channels 66, and provide a reduced contact surface area within the treatment lumen 34. Similar to the inner surface 64 of FIG. 2, the reduced contact surface area reduces the friction between the treatment lumen 34 and balloon catheter 24, improving treatment device passage performance of the guide catheter 22. The geometrically shaped inner layer 50 may be used in a guide catheter 22 having a braided middle layer 52, or alternatively, may be used in braidless guide catheter construction as shown in FIGS. 3 and 4.

Additionally, channels 66 aid in dye delivery to the coronary. As a treatment device, such as balloon catheter 24, is passed through treatment lumen 34, the treatment device may block the treatment lumen 34 of catheter 22, preventing dye from advancing past the treatment device and into the coronary artery. The channels 66 provide channels for dye to flow past the treatment device and into the coronary artery, for improved visualization of the catheter procedure. Additionally, channels 66 provide fluid channels which lubricate the treatment device as it passes through guide catheter 22.

Channels 66 in inner layer 50 also aid in perfusion of blood past the treatment device and into the coronary artery. When the distal end 32 soft tip 38 of guide catheter 22 is engaged within the ostium of the coronary to receive treatment, blood flow into the coronary is occluded or partially limited. Perfusion openings 40 provide a path for blood to flow into the treatment lumen 34, through guide catheter 22, and into the coronary artery. As a treatment device, such as balloon catheter 24, passes through the treatment lumen 34 of guide catheter 22, the balloon catheter 24 may block the treatment lumen 34. Channels 66 on inner layer 50 provide channels for blood perfusion between perfusion openings 40 and the coronary artery. Additionally, capillary action further facilitates the blood flow through the channels 66 channels.

Figure 5:
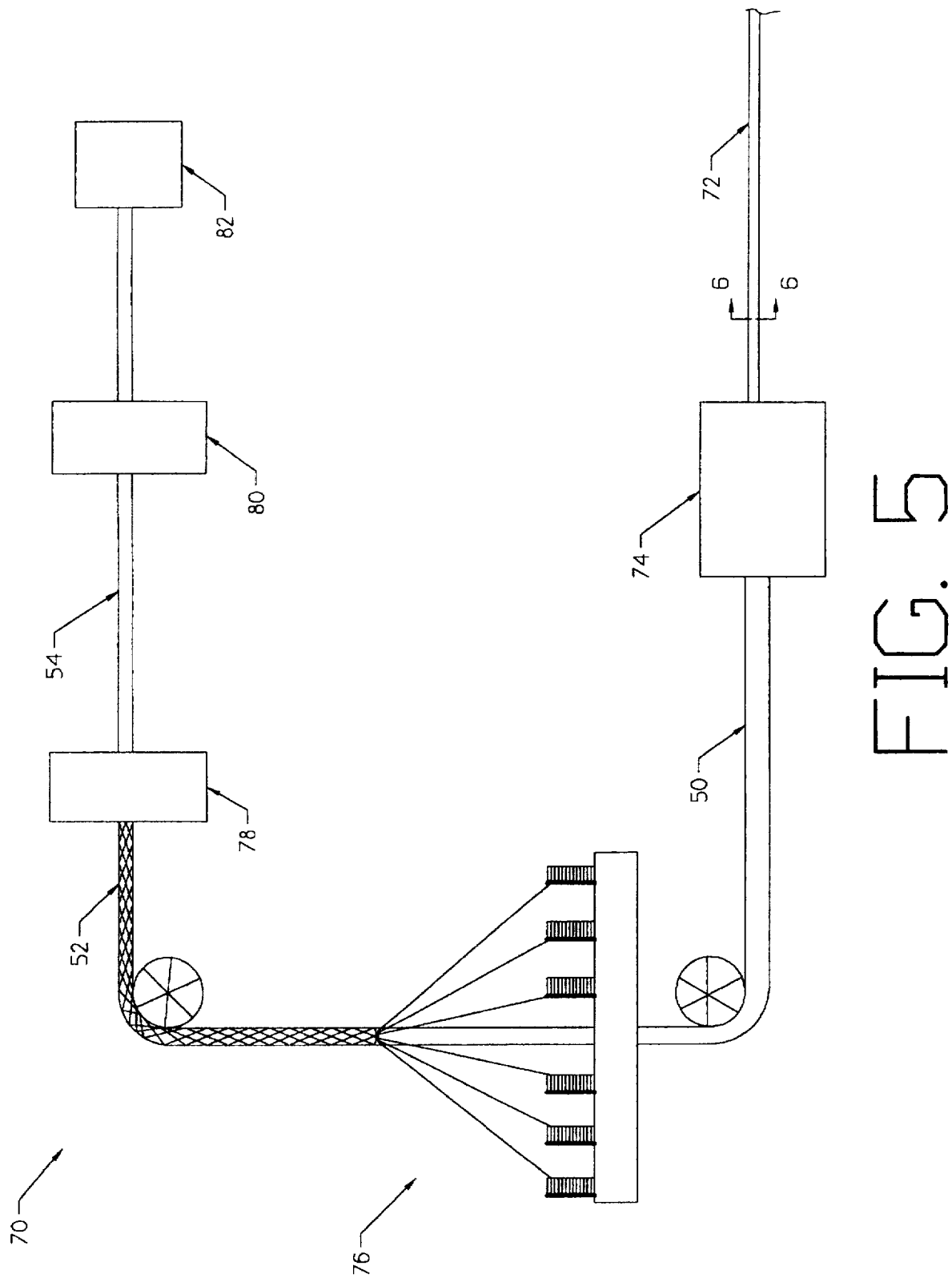
FIG. 5 is a schematic view illustrating a method of manufacturing the guide catheter shown in FIG. 1 in accordance with the present invention.

FIG. 5 shows a schematic view of one preferred embodiment of a guide catheter method of construction in accordance with the present invention, generally at 70, for manufacturing guide catheter 22 shown in FIGS. 1 and 2. As previously discussed herein, guide catheter 22 is formed of a multi-layered construction, which includes inner layer 50, middle layer 52, and outer layer 54.

Inner layer 50 is formed by passing a mandrel 72 through a first extruder 74. First extruder 74 extrudes a thin inner layer 50 of a suitable polymeric material, as previously discussed herein, onto mandrel 72 using a commonly known conventional extrusion process. Guide catheter 22 is cooled and proceeds through a braiding machine 76 for braiding middle layer 52 onto inner layer 50. In one preferred embodiment, braiding machine 76 tightly braids or helically wraps strands of stainless steel wire onto inner layer 50 to form middle layer 52.

Guide catheter 22 passes through second extruder 78 for extrusion of outer layer 54 over middle layer 52 and inner layer 50. In one preferred embodiment, a polymeric material, such as polyether block amide (PEBA), is extruded to form outer layer 54. Puller 80 continues to pull guide catheter 22 through the catheter construction process, including past cutters 82 for cutting the spooled length of guide catheter 22 into desired guide catheter lengths. The mandrel 72 is then removed.

In one preferred embodiment, mandrel 72 is formed of a silver-coated copper wire. Mandrel 72 forms guide catheter 22 in a tubular shape, and is sized such that the later removal of the mandrel 72 will provide guide catheter 22 with a lumen sufficiently sized to carry desired catheter devices.

Figure 6:
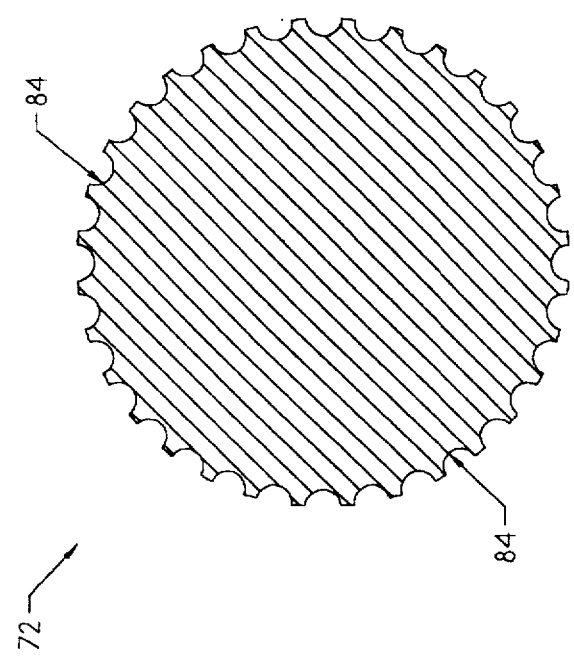
FIG. 6 is a cross-sectional view of the mandrel taken along line 6—6 of FIG. 5.

Referring to FIG. 6, a cross section of mandrel 72 taken along lines 6—6 of FIG. 5 is shown. Mandrel 72 includes an outer surface 84, which is geometrically shaped, for providing a geometrically shaped inner surface 64 to inner layer 50. The design of outer layer surface 84 is the exact opposite of the channels 66 that it imprints on inner surface 64 of inner layer 50.

Figure 7:
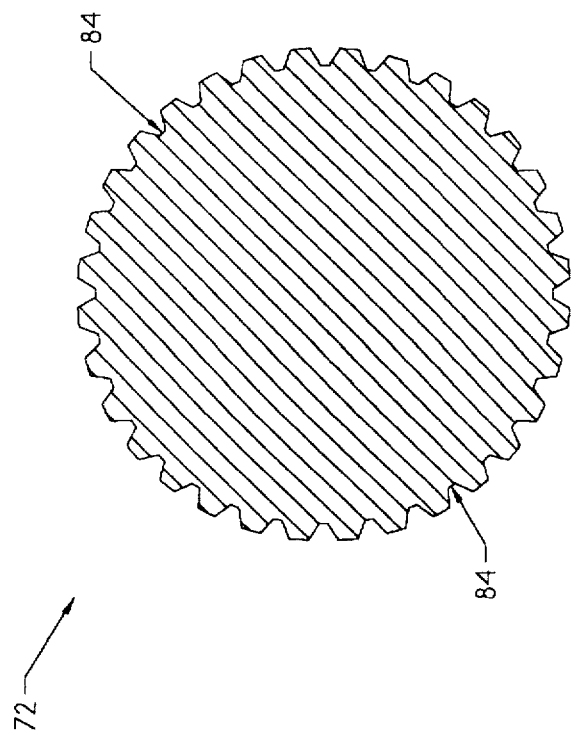
FIG. 7 is a cross-sectional view of an alternative design of the mandrel.

As inner layer 50 is extruded over mandrel 72, and cools, the inner layer 50 inner surface 64 takes on the desired geometrical configuration of mandrel 72. The mandrel 72 shown in FIG. 6 corresponds to the inner surface 64 design of inner layer 50 shown in FIG. 2. Referring to FIG. 7, the outer surface 84 is geometrically configured to correspond to the geometrical design of the inner surface 64 of inner layer 50 shown in FIG. 3.

It is also recognized that a geometrically configured inner surface 64 may be accomplished through free extrusion of guide catheter 22. In this embodiment, guide catheter 22 would be freely extruded over a dye having a desired geometrical configuration, similar to that of mandrel 72 shown in FIGS. 6 and 7 to form channels 66 in inner surface 64.

Yet another embodiment of the present invention includes a guide catheter method of construction which can be similar to the guide catheter method of construction shown in FIG. 5, without first extruder 74. Layer 52 is directly braided onto mandrel 72, which has a geometrically configured outer surface. Mandrel 72 is passed through braiding machine 76 for braiding layer 52 directly onto mandrel 72. The braiding machine 76 tightly braids or helically wraps strands directly onto mandrel 72 over the geometrically configured surface having channels contained therein. The braid is positioned on the peaks of the channeled mandrel 72.

Guide catheter 22 passes through extruder 78 for extrusion of layer 54 over braided layer 52 and mandrel 72. In one preferred embodiment, a polymeric material such as polyether block amide (PEBA) is extruded to form layer 54. As layer 54 is extruded over mandrel 72 having braided layer 52, the polymeric material "wicks" or extends underneath braided layer 52, filling the channels in mandrel 72. With this embodiment, a guide catheter 22 is formed having a braided construction with a geometrically configured inner surface using a single-pass extrusion process.

By directly braiding layer 52 onto mandrel 72, a single-pass extrusion process may be used. With this process, the braided layer 52 moves closer to the coaxial center of the catheter shaft 28, increasing kink resistance. Additionally, the treatment lumen 34 inner surface has a unique geometric configuration which decreases resistance and allows for easy passage of treatment devices through the catheter treatment lumen 34. Additionally, a kink resistant guide catheter 22 is formed using a more cost efficient one-pass extrusion manufacturing process.

Figure 8:
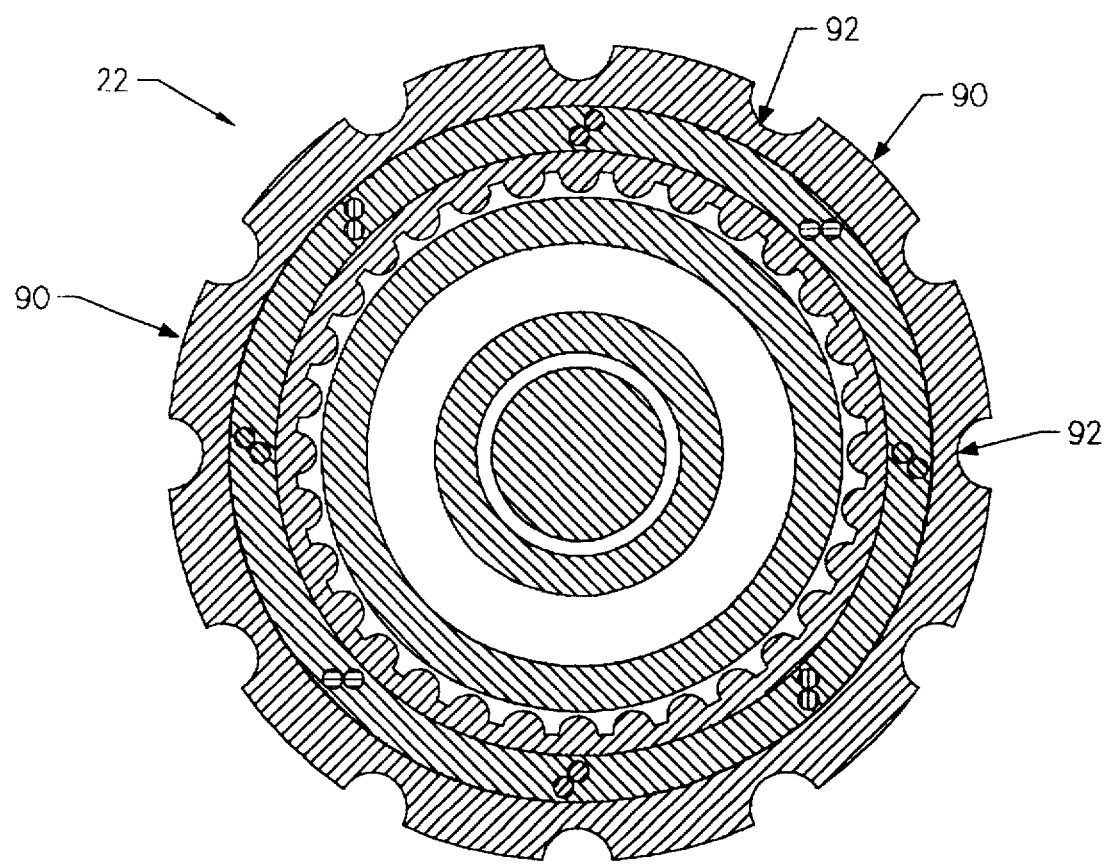
FIG. 8 is a cross-sectional view of yet another embodiment of the catheter of the present invention.

Referring to FIG. 8, yet another embodiment of the present invention is shown. FIG. 8 is a cross section of a guide catheter having a treatment device disposed therein. The guide catheter and treatment device can be similar to guide catheter 22 and balloon catheter 24 shown in FIG. 1. The cross section is taken near the distal end 32 of shaft 28, near soft tip 38. In this embodiment, the design of the distal portion of catheter shaft 28 provides for perfusion of blood into the coronary artery without the use of perfusion openings in shaft 28.

In addition to the elements previously described herein, guide catheter 22 includes a distal perfusion section 90 for perfusion of blood into the coronary artery during ostial engagement. In one preferred embodiment, distal perfusion section 90 is formed of a soft polymeric material, such as polyether block amide (PEBA). The distal perfusion section 90 is approximately 1 inch long and includes perfusion channels 92 radially spaced about distal perfusion section 90 extending longitudinally along the exterior surface thereof. Distal perfusion section 90 may be extruded over the distal end 32 of shaft 28, or alternatively, distal perfusion section 90 may be freely extruded in the form of a tubular sleeve which is placed over the distal end 32 of shaft 28 and bonded to the shaft 28 using adhesives.

Conventional catheter designs utilize side holes or perfusion openings near the distal portion of the catheter shaft to improve blood perfusion into the coronary artery during catheter engagement. When the catheter tip engages the ostium of the coronary to receive treatment, it can block the blood passage into the artery. The side holes or perfusion openings allow blood to enter the catheter lumen, flow through the lumen, and into the coronary artery. The use of perfusion openings require the blood to be forced through the perfusion openings at 90 degrees and into the catheter lumen, then past treatment devices positioned within the catheter lumen before reaching the coronary artery. Such a perfusion path for blood flow does not provide optimal perfusion.

Additionally, perfusion openings result in stress points in the catheter shaft due to the absence of catheter material at those locations. The stress points can result in catheter shaft kink or failure at the side hole locations. Perfusion openings also allow dye to dissipate out of side holes rather than into the coronary resulting in low dye and coronary visualization. Additionally, catheter designs require that hospitals and clinics inventory catheters with both perfusion side holes and non-side hole catheters.

The perfusion channels 92 of the present invention eliminate the need for side holes or perfusion openings in the external distal wall of the catheter shaft. The perfusion channels 92 provide improved channeling of blood flow past the distal end of the catheter shaft during ostial engagement, and into the coronary artery. Perfusion is no longer affected by the number and size of the treatment device located within the guide catheter 22 lumen.

Additionally, the location of perfusion channels 92 along the outside of guide catheter 22 allow for more efficient dye delivery through the guide catheter 22 treatment lumen 34 into the coronary artery. Without perfusion openings, the dye delivery is more concentrated and focused into the coronary artery. Additionally, perfusion channels 92 could be located on all catheter designs and sizes, eliminating the need for doubling of inventory and doubling of manufacturing for providing both side hole and non-side hole catheter models.

Figure 9:
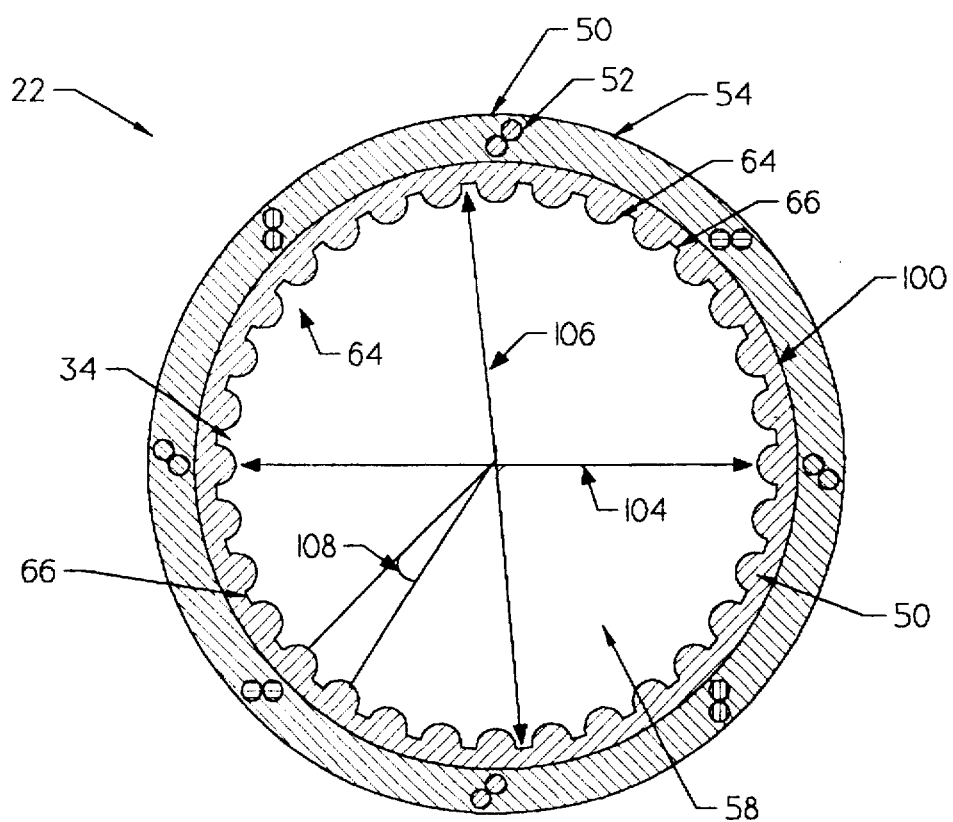
FIG. 9 is a cross-sectional view of one application of the catheter of the present invention having microgroove channels located along the interior lumen therein.

In FIG. 9, one preferred embodiment of the guide catheter in accordance with the present invention is shown at 22. The guide catheter 22 can be similar to the guide catheter 22 as previously described herein.

The guide catheter 22 includes the first inner layer 50 having a generally tubular or circular outer circumference 100 and the geometrically configured inner surface 64, including a plurality of longitudinally extending microchannels 66 as previously described herein. The microchannels 66 are spaced axially about the inner surface 64. In one embodiment, the microchannels 66 extend longitudinally the entire length of the catheter shaft 28. In another embodiment, the microchannels 66 extend longitudinally near the distal end 32 of the catheter shaft 28, from a location proximate the distal end 32.

In the exemplary embodiment shown, the inner layer 50 is formed of a polymeric material of a relatively low durometer, preferably having a shore hardness rating of less than 72 durometers. The geometrically configured inner surface 64 includes 33 microchannels 66 extending longitudinally along the wall of the shaft 28. Adjacent each microchannel 66 is a raised microportion 102. The raised microportion is very small in height. The raised microportion 102 can have a height of less than one hundredth of an inch when measured relative to a reference plane defined by the bottom of an adjacent microchannel 66. In the exemplary embodiment shown, inner layer 50 includes a minor inside diameter 104 and a major inside diameter 106. The minor inside diameter 104 is defined by the height of the raised micro portions 102, and the major inside diameter 106 is defined by the bottom of the microchannels 66. In the exemplary embodiment shown, the minor inside diameter 104 is approximately 0.084 inches and the major inside diameter 106 is approximately 0.087 inches , resulting in a raised microportion 102 having a height of approximately 0.003 inches. Further, the raised portions 102 can have a peak-to-peak spacing of 11.25 degrees (indicated at 108), resulting in a peak-to-peak distance of 0.00824 inches ($S=r\theta$), with a microchannel 66 width of approximately 0.0067 inches.

As previously stated herein, the geometrically configured inner surface 64 having microchannels 66 reduces the friction between catheter 22 and a treatment device moving therethrough, while maximizing the available space for passage of treatment devices therethrough. The geometrically configured inner surface 64 eliminates the need for a lubricous polymer, such as polytetrafluoroethylene, as part of the inner layer 50 material. The geometrically configured inner surface 64 significantly lowers manufacturing costs by eliminating special extrusion processes associated with providing guide catheter 22 with a polytetrafluoroethylene inner layer and etching. Additionally, geometrically configured inner surface 64 eliminates problems associated with adherence of polytetrafluoroethylene to catheter shaft materials.

The geometrically configured inner surface 64 having microgrooves 66 improves the performance of catheter shaft 28, allowing a larger minor inside diameter 104 for passage of treatment devices therethrough. In conventional catheters, a lubricous polymer or polytetrafluoroethylene inner layer accounts for approximately 20 percent of the thickness of the guide catheter wall. With the present invention, a lubricous polymer inner layer is no longer necessary, allowing for a greater minor inside diameter 104. Other less desirable catheter configurations utilize rigid, splined internal walls which provide support to the catheter, but greatly sacrifice the available space necessary for easy passage of treatment devices therethrough.

Additionally, since a lubricous polymer inner layer is no longer necessary, additional shaft material may be used for guide catheter 22. The higher volume of shaft material increases catheter curve retention, backup support, and radiopacity properties. Alternatively, the absence of a lubricous polymer inner layer may allow for maximizing the size of treatment lumen 34 relative to guide catheter 22, allowing for slidable reception of larger treatment devices within a catheter having a smaller outside diameter.

The microchannels 66 result in raised portions 102 of very minimal height, such that they do not alter the general structural properties of the guide catheter 22. The microchannels 66 allow for a conventional braided catheter design, without increasing the outside diameter of guide catheter 22, while maximizing the minor inside diameter 104 of guide catheter 22 for passage of treatment devices therethrough.

It will be understood, that this disclosure is, in many respects, only illustrative. Changes may be made in details, particularly in matters of shape, size, material, and arrangement of parts without exceeding the scope of the invention. Accordingly, the scope of the invention is as defined within the language of the appended claims.

What is claimed is:

1. In a braided catheter having a generally elongate shaft having a proximal end and a distal end, with a lumen extending longitudinally between the proximal end and the distal end, the shaft including a first inner layer, a second braided layer carried by the first inner layer, and a third outer layer coupled to the first inner layer, the improvement comprising:

the first inner layer having a tubular shape and formed of a polymeric material having a shore hardness of less than 72 durometer, the first inner layer including a generally circular outer surface and a geometrically configured inside surface having a plurality of longitudinal microchannels spaced radially about the inside surface, the geometrically configured inner surface allowing easy passage of a treatment device therethrough, while maximizing the inside diameter of the catheter.

2. The braided catheter of claim 1, the improvement further comprising wherein the geometrically configured inside surface includes a plurality of longitudinal raised micro-portions, each micro-portion being adjacent a microchannel.

3. The braided catheter of claim 2, the improvement further comprising wherein a reference surface is defined by the bottom of each microchannel, and wherein each raised portion has a height relative to the reference portion of less than one hundredth of an inch relative to the reference surface.

4. The braided catheter of claim 1, wherein the microchannels extend longitudinally along the length of the elongate shaft.

5. The braided catheter of claim 1, wherein the microchannels extend longitudinally along a portion of the elongate shaft located proximate the distal end of the elongate shaft.

6. The braided catheter of claim 1, wherein there are more than twenty microchannels.

7. The braided catheter of claim 1, wherein the first inner layer has a shore hardness of less than 65 durometers.

8. A braided catheter having a generally elongate shaft having a proximal end and a distal end, with a lumen extending longitudinally between the proximal end and the distal end, the braided catheter comprising:

a first inner layer;

a second braided layer carried by the first inner layer;

a third outer layer coupled to the first inner layer; and means for maximizing the diameter of the lumen including the first inner layer having a tubular shape and formed of a polymeric material having a shore hardness of less than 72 durometer, the first inner layer including a generally circular outer surface and a geometrically configured inside surface having a plurality of longitudinal microchannels spaced radially about the inside surface, the geometrically configured inner surface allowing easy passage of a treatment device therethrough, while maximizing the inside diameter of the catheter.

9. The braided catheter of claim 8, the improvement further comprising wherein the geometrically configured inside surface includes a plurality of longitudinal raised micro-portions, each micro-portion being adjacent a microchannel.

10. The braided catheter of claim 8, the improvement further comprising wherein a reference surface is defined by the bottom of each microchannel, and wherein each raised portion has a height relative to the reference portion of less than one hundredth of an inch relative to the reference surface.

11. The braided catheter of claim 8, wherein the microchannels extend longitudinally along the length of the elongate shaft.

12. The braided catheter of claim 8, wherein the microchannels extend longitudinally along a portion of the elongate shaft located proximate the distal end of the elongate shaft.

13. The braided catheter of claim 8, wherein there are more than twenty microchannels.

* * * * *